United States Patent
Miyakawa et al.

(10) Patent No.: US 7,348,585 B2
(45) Date of Patent: Mar. 25, 2008

(54) SURFACE INSPECTION APPARATUS

(75) Inventors: Kazuhiro Miyakawa, Tokyo (JP);
Yoichiro Iwa, Tokyo (JP); Akihiko Sekine, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 222 days.

(21) Appl. No.: 11/135,478

(22) Filed: May 24, 2005

(65) Prior Publication Data

US 2005/0270522 A1    Dec. 8, 2005

(30) Foreign Application Priority Data

Jun. 3, 2004 (JP) .............................. 2004-165671

(51) Int. Cl.
*G01N 21/86* (2006.01)
(52) U.S. Cl. ................. 250/559.41; 356/237.1
(58) Field of Classification Search ........... 250/559.41, 250/559.29, 559.3, 559.45; 356/237.2–237.5, 356/239.7, 239.71, 237.1
See application file for complete search history.

(56) References Cited

U.S. PATENT DOCUMENTS

| | | | |
|---|---|---|---|
| 5,835,220 A * | 11/1998 | Kazama et al. | 356/369 |
| 5,892,224 A * | 4/1999 | Nakasuji | 250/310 |
| 6,636,310 B1 * | 10/2003 | Ben-Dov et al. | 356/601 |
| 2002/0041374 A1 * | 4/2002 | Ohshima et al. | 356/237.2 |
| 2002/0180959 A1 * | 12/2002 | Nakajima et al. | 356/237.1 |
| 2003/0020917 A1 * | 1/2003 | Mundt et al. | 356/446 |
| 2004/0042001 A1 * | 3/2004 | Vaez-Iravani et al. | 356/237.2 |
| 2004/0061851 A1 * | 4/2004 | Isozaki et al. | 356/237.3 |

FOREIGN PATENT DOCUMENTS

JP        11-153549 A        6/1999

\* cited by examiner

*Primary Examiner*—Kevin Pyo
*Assistant Examiner*—Kevin Wyatt
(74) *Attorney, Agent, or Firm*—Buchanan Ingersoll & Rooney PC

(57) ABSTRACT

A surface inspection apparatus of the present invention includes an irradiation optical unit having a multibeam irradiation optical unit for converging and irradiating multiple beams upon a surface of an object to be inspected; a detector which has a light-condensing optical unit including light-sensitive elements for respectively receiving the multiple beams reflected by the surface of the inspecting object; and a processor which obtains a plane-coordinate-position of a position to be irradiated and detected at a reference height position based on a difference between light-receiving reference positions of each of the light-sensitive elements when assumed that the irradiated and detected position of the inspecting object is at the reference height position and actual light-receiving positions of each of the light-sensitive elements, according to a result of analysis and process of surface state information.

18 Claims, 10 Drawing Sheets

SURFACE INSPECTION APPARATUS

BACKGROUND OF THE INVENTION

1. Field of the Invention

The present invention relates to an improvement in a surface inspection apparatus for detecting a state of a surface of an object to be inspected.

This application claims priority under 35 U.S.C. § 119 to Patent Application Serial No. 2004-165671 filed in Japan on Jun. 13, 2005, the contents of which are incorporated herein.

2. Description of the Related Art

Heretofore, there has been known a surface inspection apparatus configured to detect a position of a foreign substance or a flaw or the like existing on a surface of an object to be inspected in a height-direction of the inspecting object, so as to detect the position of the foreign substance or the flaw or the like existing on the surface of the inspecting object accurately even when there is a warpage in the inspecting object (for reference, see JP-A 11-153549).

As shown in FIG. 1 for example, such a surface inspection apparatus is provided with an irradiation optical unit 3 for irradiating irradiation light P1 emitted from an irradiation light source 1 onto a wafer 2 as the inspecting object, a light-receiving optical unit 5 having a light-sensitive element 4 for receiving scattered light P2 of the irradiation light P1 irradiated from the irradiation optical unit 3 that is scattered by the foreign substance or the flaw or the like existing on a surface S of the wafer 2 and converting the received scattered light P2 into photoelectric conversion signals, and a light-receiving optical unit 7 having a light-sensitive element 6 for receiving specular reflection light P3 of the irradiation light P1 irradiated from the irradiation optical unit 3 that is specular-reflected from the surface S of the wafer 2 and converting the received specular reflection light P3 into photoelectric conversion signals.

The wafer 2 is displaced relative to the irradiation optical unit 3 and the light-receiving optical units 5 and 7 by using a rotational driving mechanism 8 and a linear movement mechanism 9 which are as relative displacement means. The rotational driving mechanism 8 and the linear movement mechanism 9 have a driving motor, respectively.

As shown in FIG. 2, according to such a surface inspection apparatus, when representing a surface of the wafer 2 located on a reference height Z1 by a symbol S and representing a surface of the wafer 2 in which a height is deviated by $\Delta Z$ in a height-direction (Z-direction) relative to the reference height Z1 by a symbol S', and assuming that the specular reflection light P3 from a detecting position (irradiated detecting position) y1 at the time when a foreign substance (flaw) 10 is located on the surface S enters a light-receiving reference position Q0 of the light-sensitive element 6, a light-receiving position of the light-sensitive element 6 to which specular reflection light P3' from the surface S' of the wafer 2 enters will be a position Q1 deviated relative to the light-receiving reference position Q0 by $\Delta S$. Accordingly, since there is a certain relation between the amount of deviation $\Delta S$ and the amount of deviation $\Delta Z$, an amount of deviation $\Delta y$ of a plane-coordinate-position y2 at the time when the surface S is deviated from the reference height Z1 by the height $\Delta Z$ as shown by the symbol S', relative to a plane-coordinate-position y1 in a radial direction as the irradiated detecting position of the foreign substance (flaw) 10 at the time when the surface S is at the position of the reference height Z1, is obtained by a following formula based on the amount of deviation $\Delta S$ and a reflection angle $\theta$:

$$\Delta y = \Delta S / \tan \theta$$

or a formula:

$$\Delta y = \Delta Z / \tan \theta$$

Therefore, the plane-coordinate-position y2 at the time when the irradiated detecting position is deviated relative to the reference height Z1 by the $\Delta Z$ is obtained by a following formula:

$$y2 = y1 - \Delta y$$

That is to say, it is possible to detect the foreign substance (flaw) 10 existing on the wafer 2 accurately even when there is the warpage in the wafer 2, by correcting the plane-coordinate position in the y-direction.

However, as shown in FIG. 3, when the surface S of the wafer 2 as the inspecting object is coarse, there is a possibility that the specular reflection light P3 of the irradiation light P1 specular-reflected from the surface S is deflected and misaligned as shown by a symbol P5 relative to a direction P4 of the specular reflection light P3 to which the irradiation light P1 (i.e. specular reflection light P3) should be reflected if there is no irregularity R, due to a local gradient caused by the irregularity R of the surface S.

Consequently, the conventional surface inspection apparatus has a problem that it is indistinguishable whether or not the irradiated detecting position of the foreign substance (flaw) 10 on the wafer 2 is deviated from the reference height position Z1.

SUMMARY OF THE INVENTION

Therefore, the present invention has been made in view of the above circumstances, and at least one objective of the present invention is to provide a surface inspection apparatus capable of distinguishing whether or not an irradiated detecting position of an object to be inspected is deviated from a reference height, even when a surface of the inspecting object is coarse.

To achieve these and other advantages and in accordance with the purpose of the invention, as embodied and broadly described herein, the invention provides a surface inspection apparatus. The surface inspection apparatus comprises an optical system including an irradiation optical unit and a light-receiving optical unit; the irradiation optical unit is adapted for irradiating irradiation light emitted from a light source onto a surface of an object to be inspected and the light-receiving optical unit is adapted for receiving scattered light of the irradiation light reflected from the surface of the object; a displacement mechanism for displacing a position to be irradiated and detected by the optical system on the surface of the object relative to the optical system; a recording unit for detecting a state of the surface of the object based on a result of light-receiving of the optical system and recording the irradiated and detected position on the surface of the object as a plane-coordinate-position; a detector for detecting an amount of deviation of the plane-coordinate-position in a height direction relative to a reference height position; and a processor for correcting the plane-coordinate-position as the irradiated and detected position based on the deviation amount detected by the detector and thereby obtaining the plane-coordinate-position, wherein the irradiation optical unit comprises a multibeam irradiation optical unit for converging and irradiating multiple beams of which optical axes of irradiation are mutually parallel upon the surface of the object; the detector comprises a light-condensing optical unit including light-sensitive elements which have mutually parallel light-receiving axes and which are adapted for respectively receiving the multiple beams reflected by the surface of the object; and the processor analyzes information on the state of the surface based on the results of receiving of the multiple beams, and obtains the plane-coordinate-position of the irradiated and detected position at the reference height position based on a difference between light-receiving reference positions of each of the light-sensitive elements when assumed that the irradiated and detected position of the object is at the reference height position and actual light-receiving positions of each of the light-sensitive elements, according to a result of the analysis of the surface state information.

Following are preferred embodiments (1) to (5) of the surface inspection apparatus according to the present invention. Any combinations thereof are considered to be preferred ones of the present invention unless any contradictions occur.

(1) The displacement mechanism comprises a rotational driving mechanism for rotating the object and a linear movement mechanism for linearly moving the object in a radial direction of the object, the irradiation optical axes are aligned in parallel in the radial direction of the object, and the light-receiving axes of the light-sensitive elements are aligned symmetrical to the irradiation optical axes in such a manner as to sandwich center of rotation of the object.

(2) Each of the light-sensitive elements is structured by an area sensor.

(3) The surface state information is information on coarse surface of the object or information on a surface distortion of the object.

(4) The surface inspection apparatus further comprises a display, wherein the processor displays a position at which a foreign substance and/or flaw is detected on the surface of the object on the display, based on the corrected plane-coordinate-position according to a result of correction.

(5) The multiple beams including a plurality of spots each having a same diameter of approximately 10 to 20 micrometers to each other are irradiated on the surface of the object in such a manner that neighboring spots of the plurality of spots are partially overlapped to each other, and length of alignment of the multiple beams from one end to the other end are approximately 100 micrometers or less.

According to the surface inspection apparatus of the present invention, it is possible to distinguish whether or not the irradiated detecting position for the foreign substance or the flaw or the like existing on the surface of the inspecting object is deviated from the reference height even when the surface of the inspecting object is coarse and even if there is a distortion in the surface, and also, it is possible to detect the amount of deviation from the reference height position even when the surface of the inspecting object is coarse by removing an influence of such coarseness. Therefore, even when the surface of the inspecting object is coarse, it is possible to remove the influence of the coarseness of the surface, and to obtain the plane-coordinate position as the detecting position of the foreign substance (flaw) accurately by correcting the plane-coordinate position.

The disclosure of Japanese Patent Application No. 2004-165671, filed on Jun. 3, 2004, including specification, drawings and claims is incorporated herein by reference in its entirety.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 7A and 7B are explanatory diagrams showing a relation among irradiation light, reflection light, irradiated detecting positions, and the spot images formed on the light-sensitive elements at the time when the surface of the inspecting object is uniformly deviated by a predetermined amount relative to a reference height position, wherein FIG. 7A is a diagram schematically showing a relation among the irradiation light, reflection light and the irradiated detecting positions when the surface of the inspecting object is uniformly deviated by the predetermined amount relative to the reference height position, and FIG. 7B is a schematic diagram for comparing and explaining a relation between the spot images formed on the light-sensitive elements at the time when the surface of the inspecting object is uniformly deviated by the predetermined amount relative to the reference height position and the spot images formed on the light-sensitive elements at the time when the surface of the inspecting object is at the reference height position.

FIGS. 8A and 8B are explanatory diagrams showing a relation among the irradiation light, the reflection light, the irradiated detecting positions, and the spot images formed on the light-sensitive elements at the time when the surface of the inspecting object is curved and the amount of deviation from the reference height position varies, wherein FIG. 8A is a diagram schematically showing a relation among the irradiation light, reflection light and the irradiated detecting positions when the surface of the inspecting object is curved and the amount of deviation from the reference height position varies, and FIG. 8B is a schematic diagram for comparing and explaining a relation between the spot images formed on the light-sensitive elements in each of the irradiated detecting positions and the spot images formed on the light-sensitive elements at the time when the surface of the inspecting object is at the reference height position.

FIGS. 10A to 10C are diagrams for explaining another embodiment of the surface inspection apparatus according to the present invention, wherein FIG. 10A is an explanatory diagram showing a state of irradiation of multiple beams onto the surface of a wafer, FIG. 10B is an explanatory diagram of a case where there is no warpage in the wafer but a distortion exists in the surface, and FIG. 10C is an explanatory diagram of a case where there is the warpage in the wafer and the distortion also exists in the surface.

DESCRIPTION OF THE PREFERRED EMBODIMENTS

Figure 1:
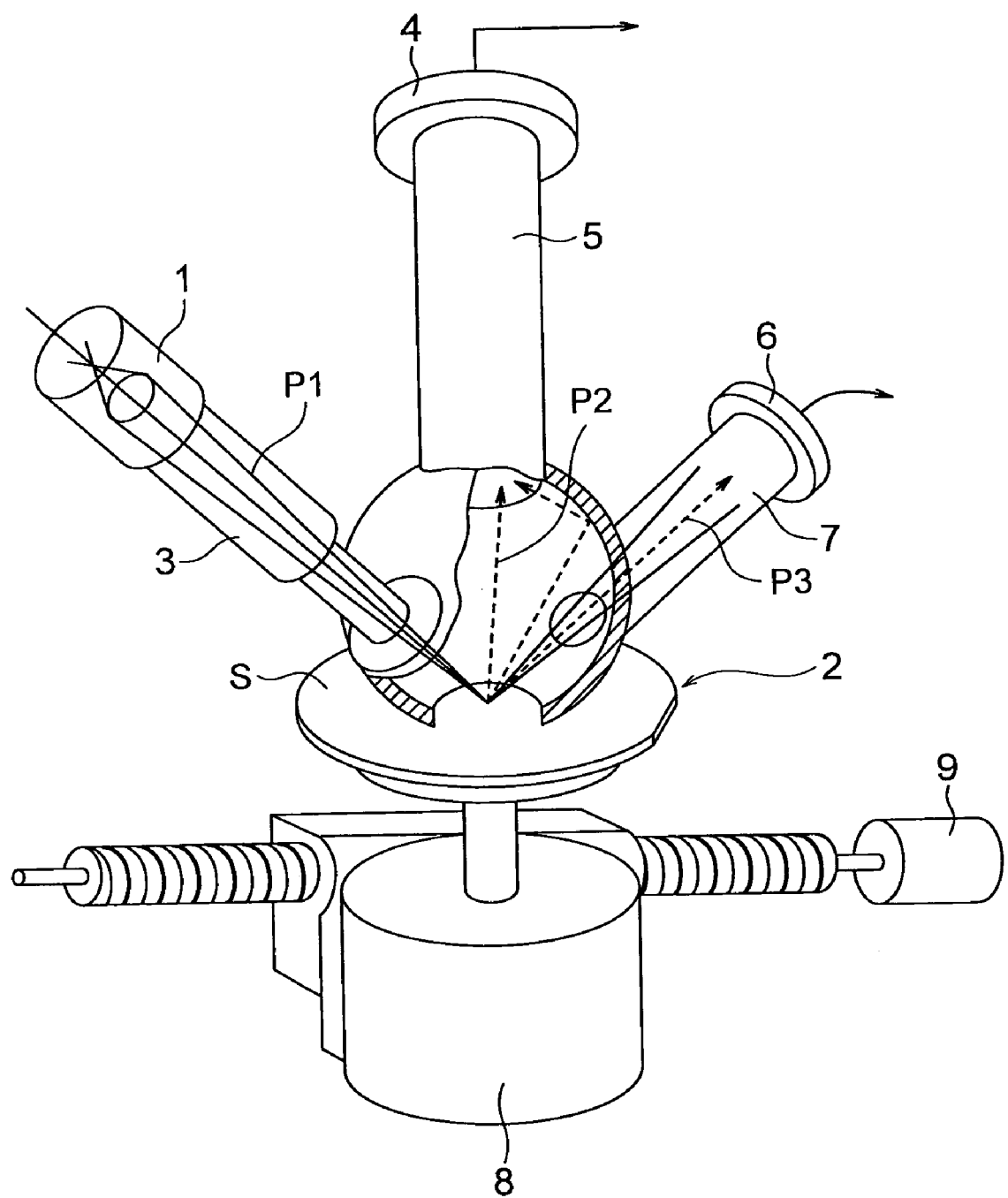
FIG. 1 is an outline diagram briefly showing a conventional surface inspection apparatus.
Figure 2:
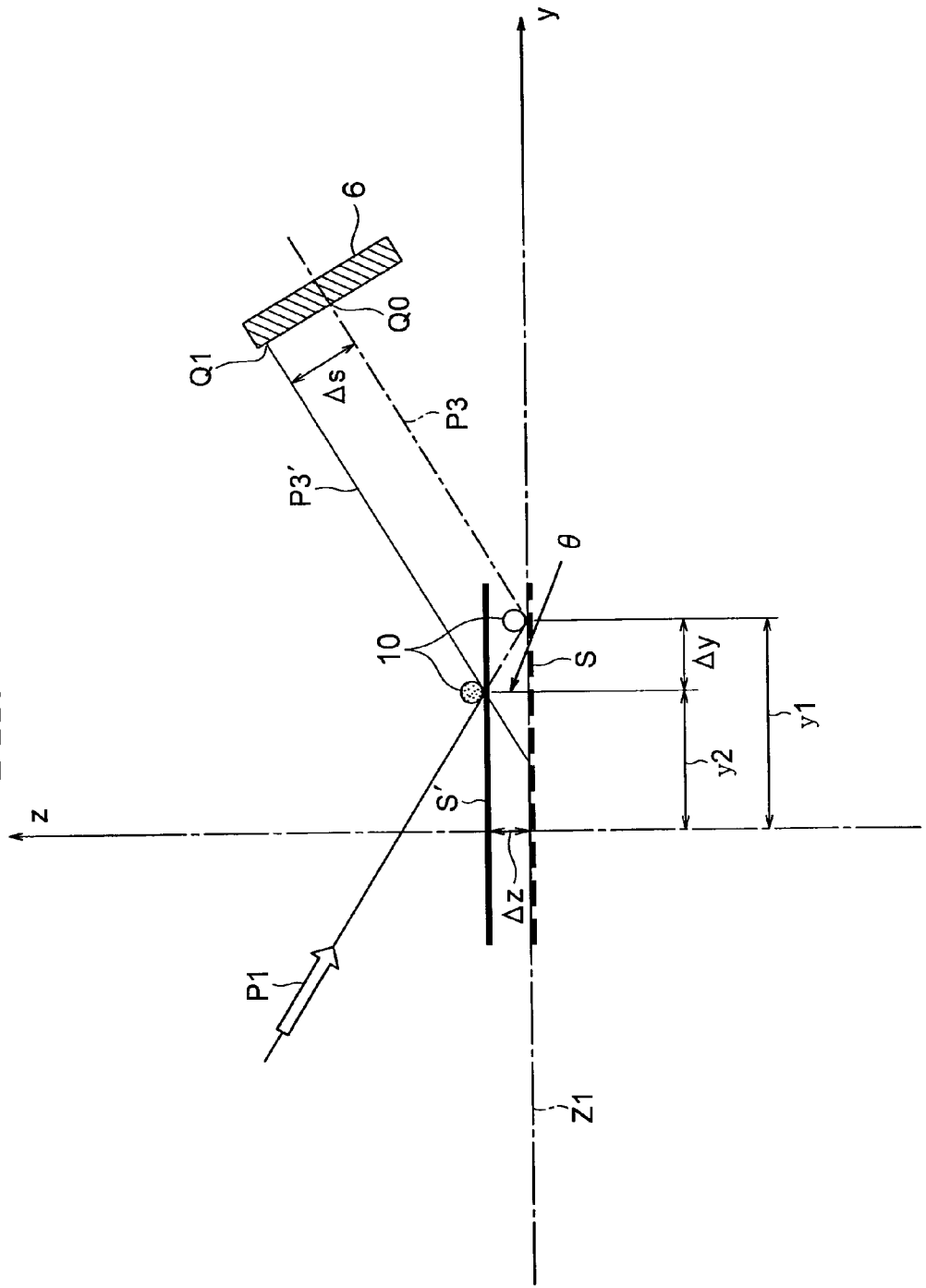
FIG. 2 is an explanatory diagram showing one example of detecting a height of an object to be inspected by the conventional surface inspection apparatus.
Figure 3:
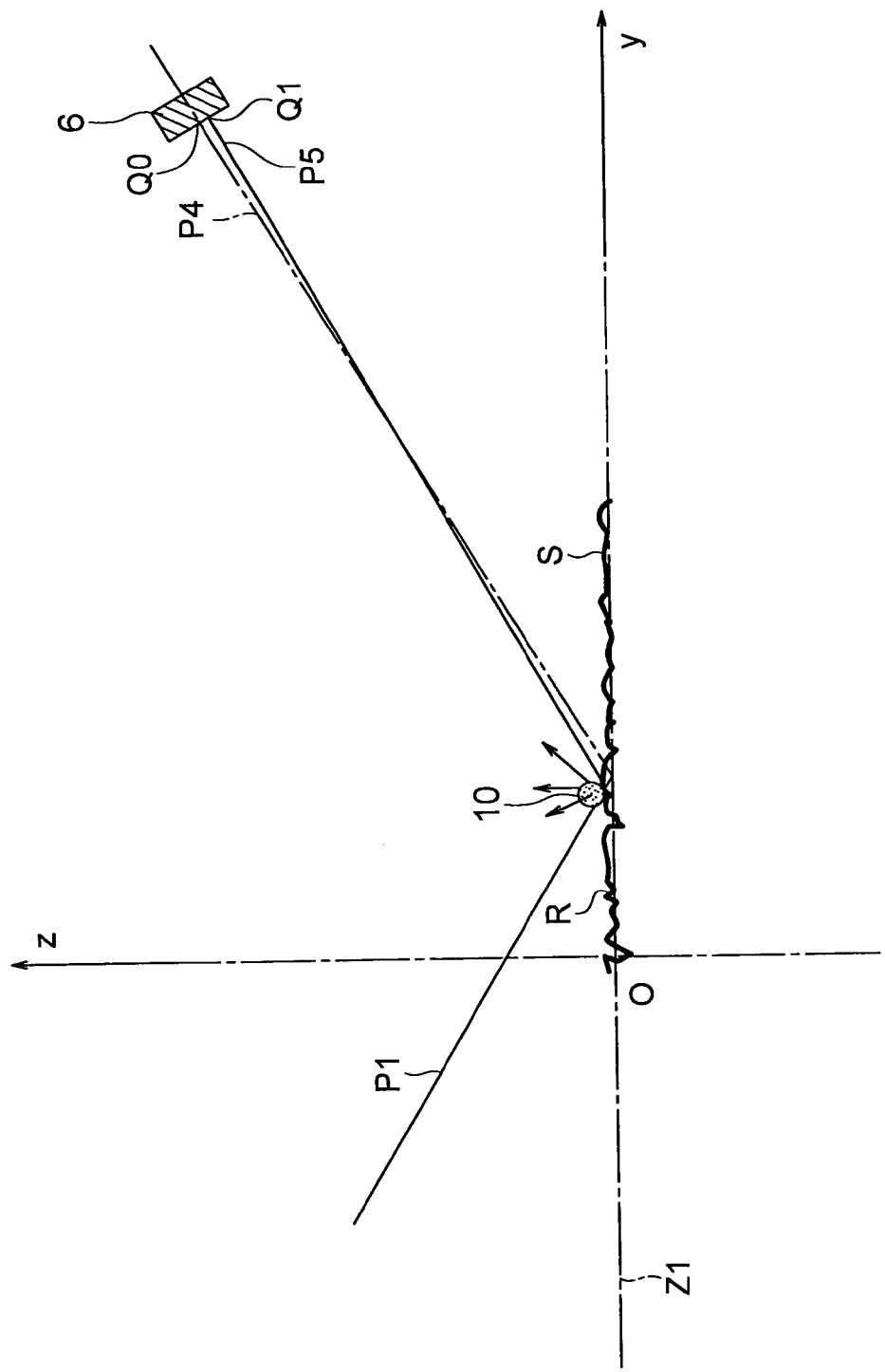
FIG. 3 is a diagram for explaining a problem of detecting the height of the inspecting object by the conventional surface inspection apparatus.

Reference will now be made in detail to the present preferred embodiments of the invention, examples of which are illustrated in the accompanying drawings. Wherever possible, the same reference numbers are used in the drawings and the description to refer to the same or like parts. The scope of the present invention, however, is not limited to these embodiments. Within the scope of the present invention, any structure and material described below can be appropriately modified.

Figure 4:
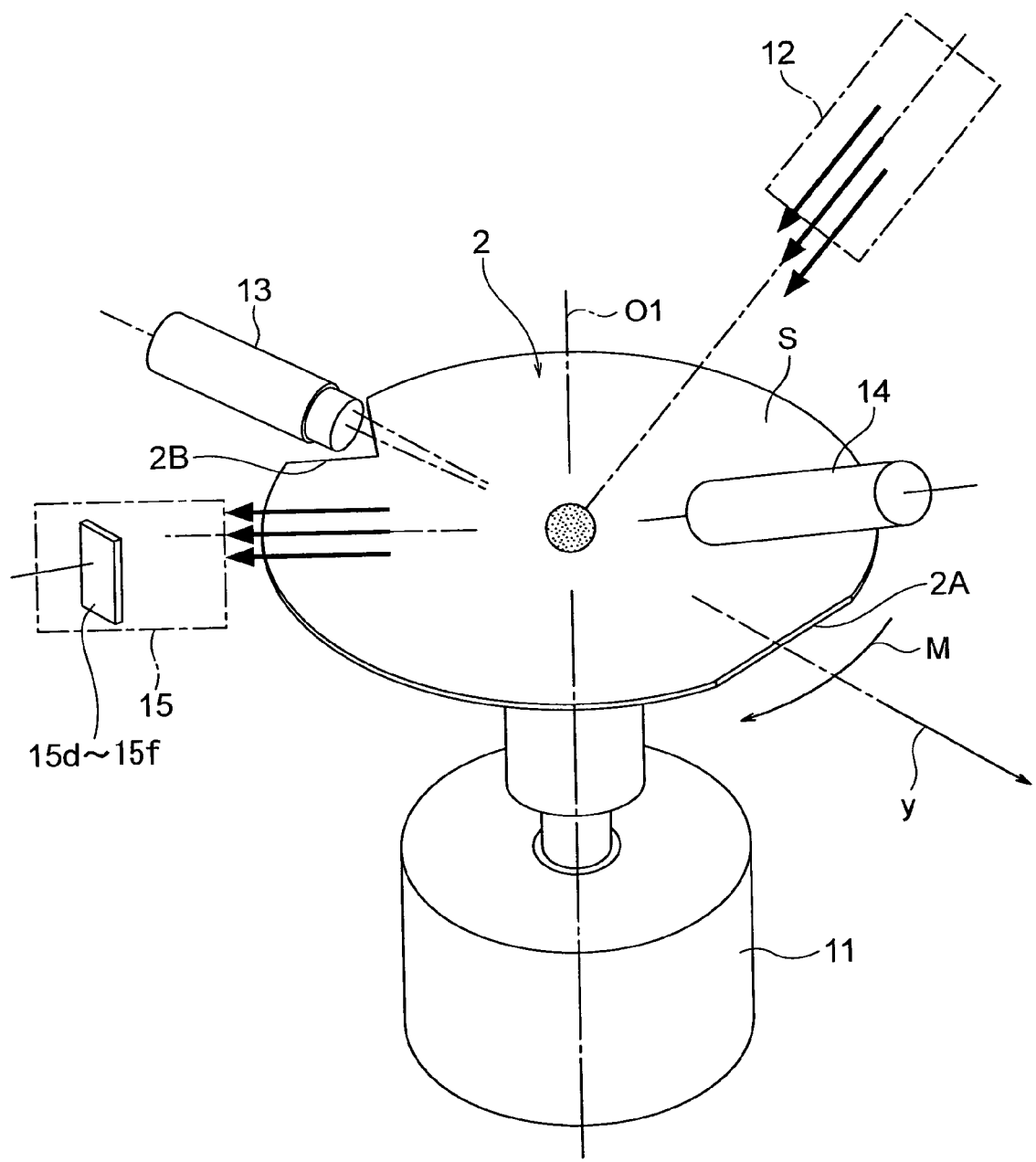
FIG. 4 is a diagram briefly showing a surface inspection apparatus according to the present invention.

FIG. 4 is a diagram briefly showing a surface inspection apparatus according to the present invention. As shown in FIG. 4, the surface inspection apparatus comprises a rotational driving mechanism 11 for rotating and driving a wafer 2 as an object to be inspected (inspecting object), an irradiation optical unit 12, light-receiving optical units 13 and 14, and a light-condensing optical unit 15. The wafer 2 is rotated and driven in an arrow M direction by the rotational driving mechanism 11 around a rotational axis 01, and is moved in an arrow y direction by a linear movement mechanism which is not shown. A detecting position (irradiated detecting position, position to be irradiated and detected) irradiated by the irradiation optical unit 12 onto a surface S of the wafer 2 is displaced relative to the optical systems 12, 13, 14 and 15 by relative displacement means (displacement mechanism) structured by the rotational driving mechanism 11 and the linear movement mechanism (illustration omitted).

Figure 5:
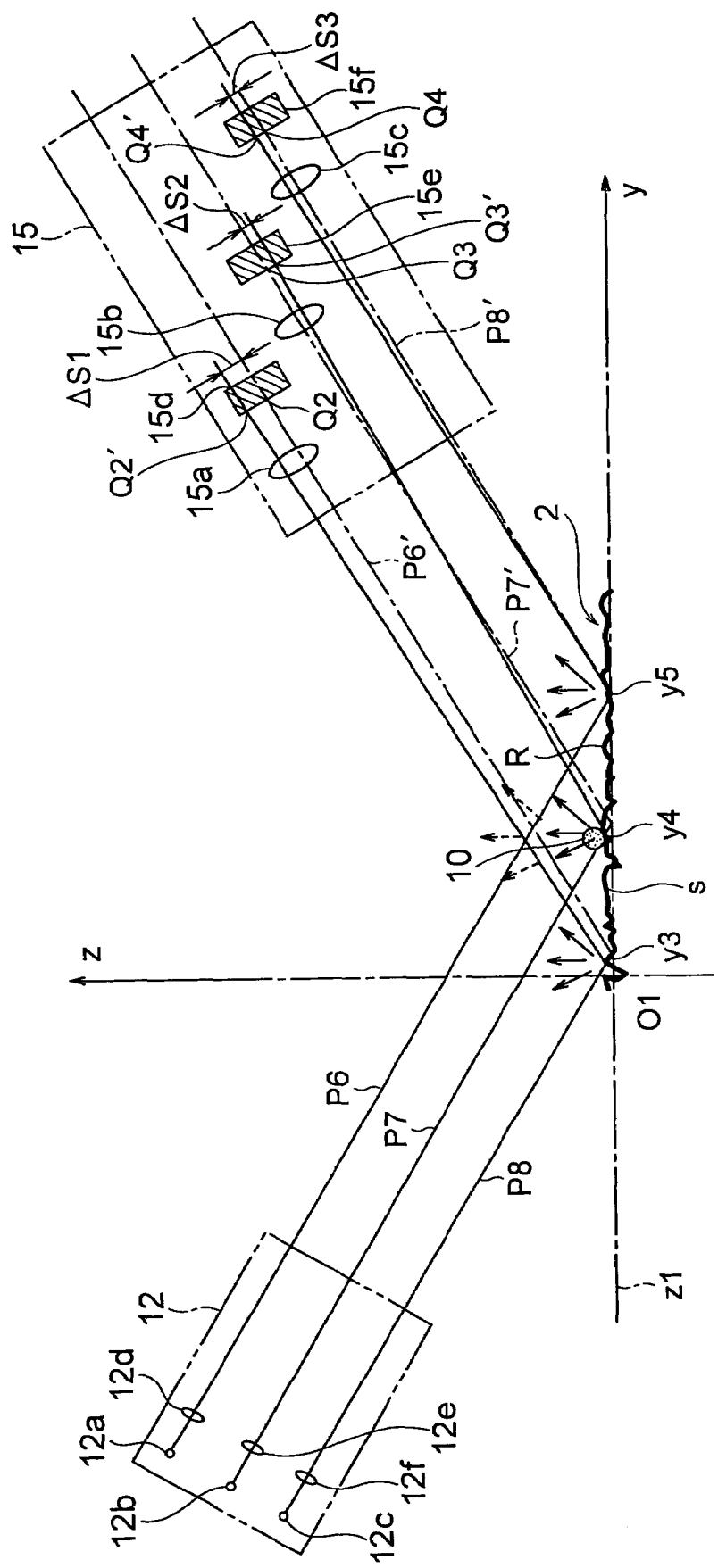
FIG. 5 is a diagram for explaining a measurement principle of detection of a coarse surface of the inspecting object by the surface inspection apparatus according to the present invention.

As shown in FIG. 5, the irradiation optical unit 12 includes a plurality of light sources. According to an embodiment of the present invention, the irradiation optical unit 12 is generally structured by, for example, three laser light sources 12a to 12c, and converging lenses 12d to 12f for condensing and shaping laser beams generated from the laser light sources 12a to 12c. and converging those laser beams onto the surface S of the wafer 2 located on a reference height position Z1 as irradiation lights P6 to P8. The irradiation optical unit 12 functions as a multibeam irradiation optical unit for irradiating a multi-laser beam (multibeam, multiple beams) as the irradiation lights P6 to P8 toward the irradiated detecting position of the surface S of the wafer 2.

Figure 9:
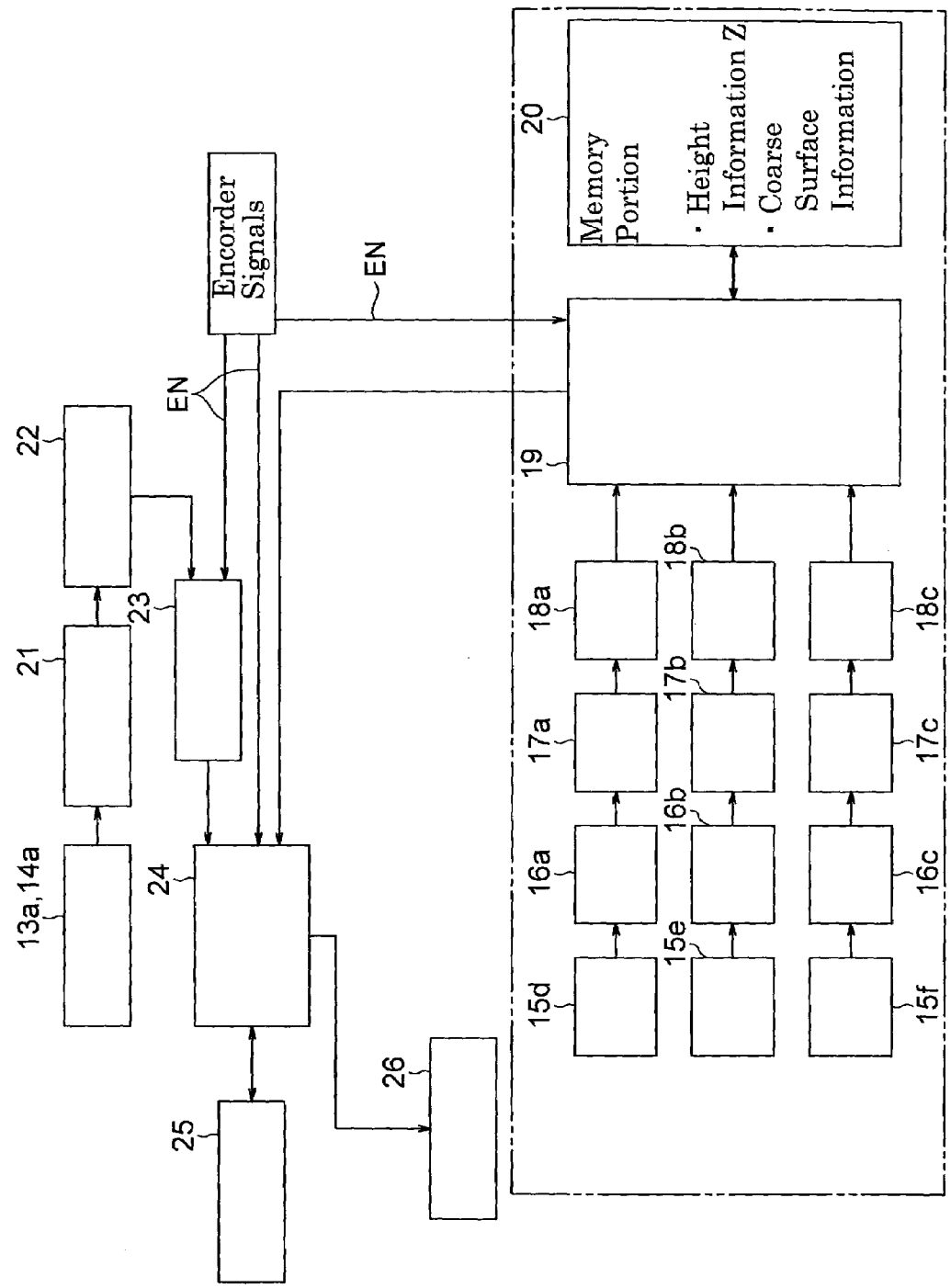
FIG. 9 is a block diagram of circuitry related to processing in the surface inspection apparatus according to the present invention.

According to an embodiment of the present invention, the light-receiving optical units 13 and 14 (see FIG. 4) are configured to receive a scattered light flux of the irradiation light emitted by the laser light source 12b for example among the laser light sources 12a to 12c, that is scattered due to a state of the surface S such as existence of a foreign substance or a flaw. As shown in FIG. 9, the light-receiving optical units 13 and 14 have photoelectric conversion elements 13a and 14a, respectively. Since structures of the light-receiving optical units 13 and 14 are the same as those of the conventional light-receiving optical units, they are not explained in detail.

According to an embodiment of the present invention, the light-condensing optical unit 15 is generally structured by condenser lenses 15a to 15c provided corresponding to the number of the laser beams of the multi-laser beam, and light-sensitive elements 15d to 15f for detecting light fluxes of receiving-lights condensed by the condenser lenses 15a to 15c.

The light-condensing optical unit 15 condenses respective reflection lights P6' to P8' of the irradiation lights P6 to P8 reflected from the irradiated detecting position of the surface S of the wafer 2. Each of the light-sensitive elements 15d to 15f is provided capable of receiving the reflection lights P6' to P8', respectively. In one embodiment of the present invention, each of the light-sensitive elements 15d to 15f is structured by an area sensor.

Optical axes of irradiation (principle rays) of the laser light source 12a to 12c are arranged to be in parallel to each other. The irradiation optical axes are aligned in parallel in a radial direction of the wafer 2. Optical axes of light-receiving (light-receiving axes) of the light-sensitive elements 15d to 15f are aligned symmetrical to the irradiation optical axes in such a manner as to sandwich the center of the rotational axis O1. In FIG. 5, symbols Q2 to Q4 represent light-receiving reference positions in a case where the surface S is ideally plane in terms of optics and also the surface S is at the reference height position Z1.

The light-condensing optical unit 15 functions a part of height direction deviation amount detecting means (height direction deviation amount detector) for detecting an amount of deviation $\Delta Z$ relative to the reference height position Z1 of the surface S.

When the surface S of the wafer 2 is at the reference height position Z1 and the surface S is not coarse and is ideally smooth in terms of optics, the irradiation lights P6 to P8 traveling on the irradiation optical axes of the irradiation optical unit 12 are specular-reflected from the surface S, and the reflection lights P6' to P8' specular-reflected from the surface S of the irradiation lights P6 to P8 are received on the light-receiving reference positions Q2 to Q4 of the light-sensitive elements 15d to 15f in such a manner that the peak is generated on the light-receiving reference positions Q2 to Q4.

However, when the surface S is coarse, or in other words, when there is irregularity R on the surface S, the irradiation lights P6 to P8 are influenced by such coarseness or the irregularity R, and hence, reflection lights of the influenced irradiation lights are received for example on light-receiving positions Q2' to Q4' which are misaligned from the light-receiving reference positions Q2 to Q4, in such a manner that the beak is generated on the light-receiving positions Q2' to Q4'.

Accordingly, it is possible to discriminate whether or not the irregularity R exists on the surface S, based on respective amounts of deviation $\Delta S1$ to $\Delta S3$ deviated from the light-receiving reference positions Q2 to Q4 of each of the light-sensitive elements 15d to 15f.

Figure 6:
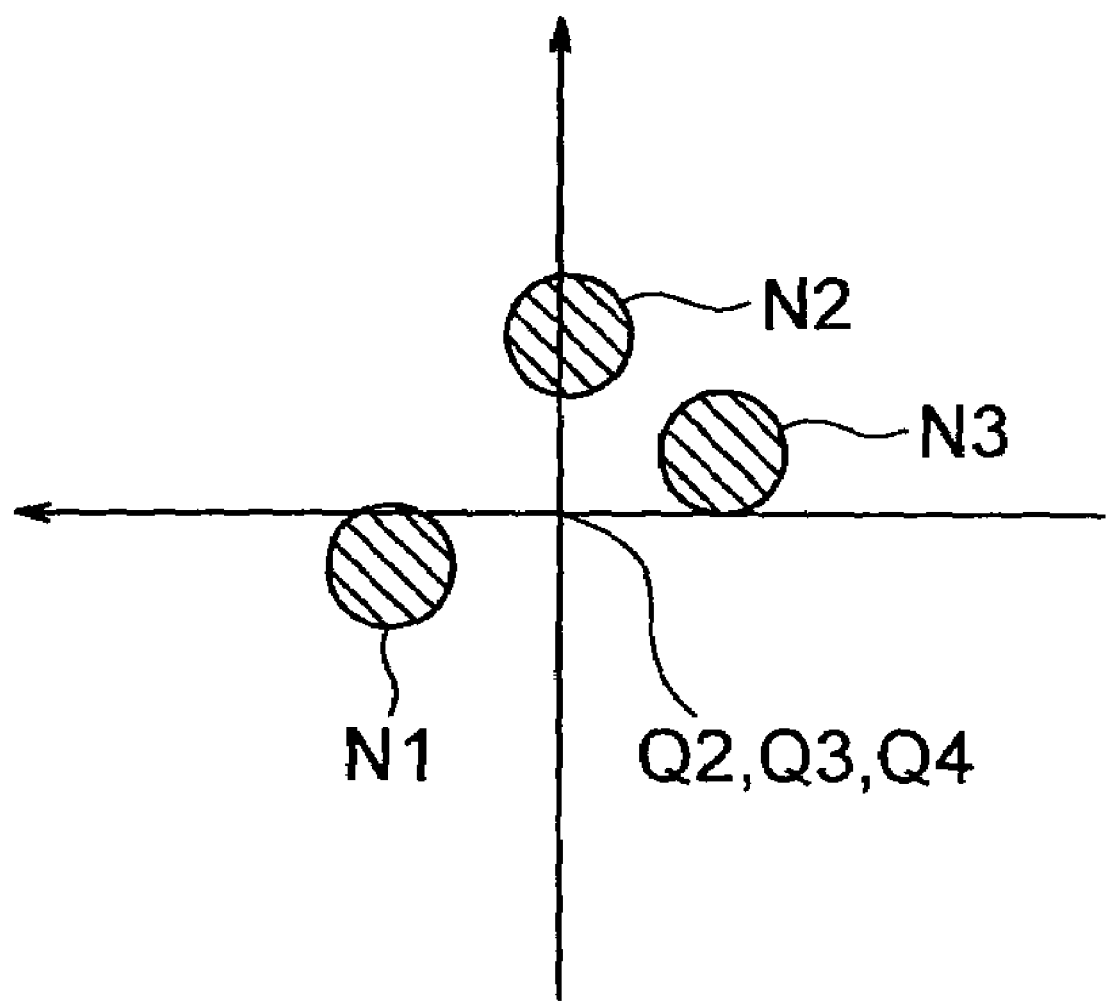
FIG. 6 is a diagram showing one example of spot images formed on light-sensitive elements according to the present invention.

Also, since the directions to which the irradiation lights P6 to P8 (i.e. the multi-laser beam) are reflected change depending upon curving directions of the irregularity R, positions where light-receiving spot images N1 to N3 are imaged on light-receiving surfaces of the light-sensitive elements 15d to 15f vary in two dimensions as shown in FIG. 6.

In FIG. 6, for example, the light-receiving spot image N1 corresponds to an spot image which is formed by the fact that the reflection-light P6' based on the irradiation light P8 reflected by a plane-coordinate-position y3 as the irradiated detecting position of the surface S is imaged on the light-sensitive element 15d, whereas the light-receiving spot image N2 corresponds to an spot image which is formed by the fact that the reflection-light P7' based on the irradiation light P7 reflected by a plane-coordinate-position y4 as the irradiated detecting position of the surface S is imaged on the light-sensitive element 15e. The light-receiving spot image N3 corresponds to an spot image formed by the fact that the reflection-light P8' which is based on the irradiation light P6 reflected by a plane-coordinate-position y5 as the irradiated detecting position of the surface S is imaged on the light-sensitive element 15f.

Figure 7A:
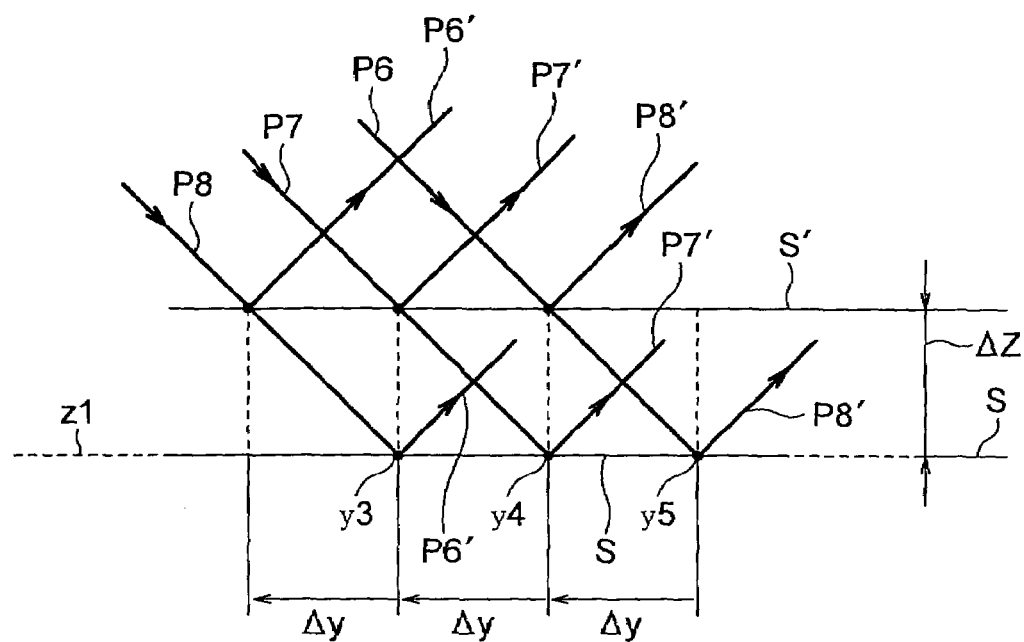

On the contrary, in a case where a surface of the wafer 2 is uniformly deviated from the reference height position Z1 by the ΔZ as shown in FIG. 7A, the irradiation lights P6 to P8 are reflected on the surface S' before the irradiation lights P6 to P8 are focused on the surface S at the reference height position Z1, and in such a case, the irradiated detecting positions in plane-coordinate-systems of the surface S' are also deviated uniformly from the irradiated detecting positions in plane-coordinate-systems of the surface S at the reference height position Z1 by Δy.

Figure 7B:
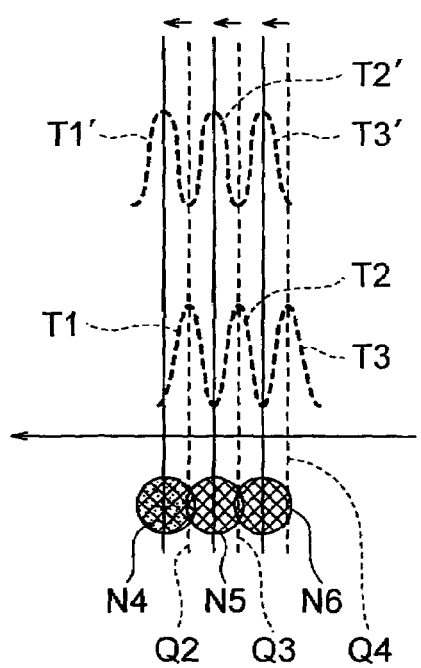

Correspondingly, the reflection lights P6' to P8' of the irradiation lights P6 to P8 are also received on the light-sensitive elements by deviating uniformly by the Δy in the same directions from the light-receiving reference positions Q2 to Q4 as shown in FIG. 7B, and hence, degrees of blur caused by the reflection lights P6' to P8' may become the same, uniformly.

In FIG. 7B, for example, a symbol N4 represents a spot image on the light-receiving surface of the light-sensitive element 15d, a symbol N5 represents a spot image on the light-sensitive element 15e, and a symbol N6 represents a spot image on the light-receiving surface of the light-sensitive element 15f.

In addition, as shown in FIG. 7B, for example, a symbol T1 represents distribution of amount of light of the spot image formed on the light-sensitive element 15d by the reflection light P6' when the surface S is at the reference height position Z1, a symbol T2 represents distribution of amount of light of the spot image formed on the light-sensitive element 15e by the reflection light P7' when the surface S is at the reference height position Z1, and a symbol T3 represents distribution of amount of light of the spot image formed on the light-sensitive element 15f by the reflection light P8' when the surface S is at the reference height position Z1.

Moreover, as shown in FIG. 7B, for example, a symbol T1' represents distribution of amount of light of the spot image formed on the light-sensitive element 15d by the reflection light P6' when the surface S is at the position deviated from the reference height position Z1 in the height direction by ΔZ, a symbol T2' represents distribution of amount of light of the spot image formed on the light-sensitive element 15e by the reflection light P7' when the surface S is at the position deviated from the reference height position Z1 in the height direction by ΔZ, and a symbol T3' represents distribution of amount of light of the spot image formed on the light-sensitive element 15f by the reflection light P8' when the surface S is at the position deviated from the reference height position Z1 in the height direction by ΔZ.

Accordingly, FIG. 7B shows that the peaks of the light amount distributions T1' to T3' are deviated in the same direction by same amount when the surface S is deviated from the reference height position Z1 in the height direction by ΔZ.

Figure 8A:
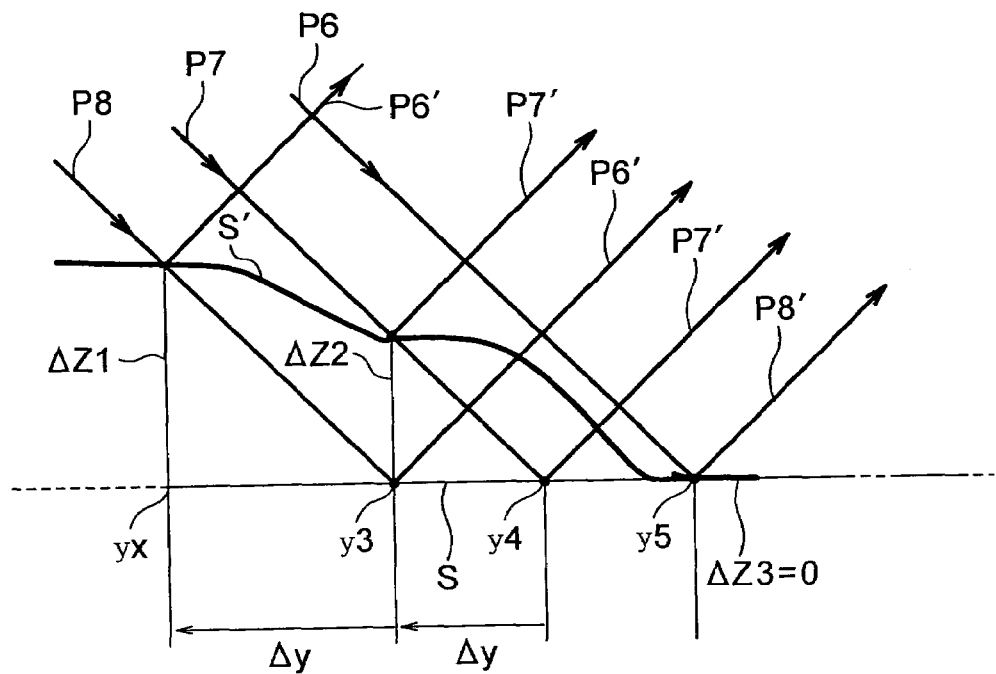

On the other hand, when the surface S' of the wafer 2 is curved as shown in FIG. 8A, and hence, for example, when an amount of deviation ΔZ1 from the reference height position Z1 at an irradiated detecting position yx of the plane-coordinate-systems of the surface S' is the largest, an amount of deviation ΔZ2 from the reference height position Z1 at the irradiated detecting position y3 of the plane-coordinate-systems of the surface S' is intermediate between the irradiated detecting position yx and an amount of deviation ΔZ3 at the irradiated detecting position y5, and the amount of deviation ΔZ3 from the reference height position Z1 at the irradiated detecting position y5 is 0 (zero), the reflection light P8' of the irradiation light P6 reflected from the irradiated detecting position y5 is received at the light-receiving reference position Q4 of the light-sensitive element 15f with an in-focus state, whereas the reflection light P7' of the irradiation light P7 reflected from the irradiated detecting position y3 is received at a position deviated from the light-receiving reference position Q3 of the light-sensitive element 15e by ΔS2, wherein the ΔS2 is proportional to the amount of deviation ΔZ2. Also, the reflection light P7' of the irradiation light P7 reflected from the irradiated detecting position y3 is imaged on the light-sensitive element 15e with an out-of-focus state.

With regard to the reflection light P6', the reflection light P6' of the irradiation light P8 reflected from the irradiated detecting position yx of the surface S is received at a position deviated from the light-receiving reference position Q2 of the light-sensitive element 15d by ΔS1, wherein the ΔS1 is proportional to the amount of deviation ΔZ1. Also, the reflection light P6' of the irradiation light P8 reflected from the irradiated detecting position yx is imaged on the light-sensitive element 15d with the out-of-focus state as shown in FIG. 8B, and the degree of blur of focus on the light-sensitive element 15d is greater than that on the light-sensitive element 15e.

Figure 8B:
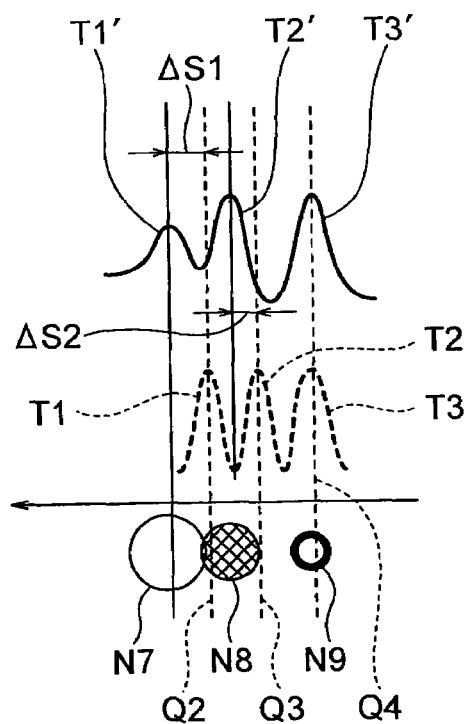

In FIG. 8B, for example, a symbol T1' represents distribution of amount of light of the spot image formed on the light-sensitive element 15d by the reflection light P6' when the surface S is at the position deviated from the reference height position Z1 in the height direction by ΔZ1, a symbol T2' represents distribution of amount of light of the spot image formed on the light-sensitive element 15e by the reflection light P7' when the surface S is at the position deviated from the reference height position Z1 in the height direction by ΔZ2, and a symbol T3' represents distribution of amount of light of the spot image formed on the light-sensitive element 15f by the reflection light P8' when the surface S is at the position deviated from the reference height position Z1 in the height direction by ΔZ3.

Accordingly, when there is a curvature or a warpage in the surface S but the surface S is smooth in terms of optics, an amount of deviation ΔS from a light-receiving reference position Q0 of each of the light-sensitive elements 15d to 15f is proportional to the amount of deviation ΔZ from the reference height position Z1, and also, the directions of deviation from the light-receiving reference position Q0 are the same. On the other hand, when there is the irregularity R on the curvature or the warpage in the surface S, the directions of deviation from the light-receiving reference position Q0 and the amounts of deviation are varied at random.

Therefore, it is possible to analyze and process information on height and information on coarse-surface, from patterns of the light amount distributions on the area sensors of the light-sensitive elements 15d to 15f.

As shown in FIG. 9, signals on the light-receiving outputted from each of the light-sensitive elements 15d to 15f are inputted into a processing circuit as recording means (recording unit). The processing circuit comprises height position detecting circuit portions 16a to 16c, analog/digital converting circuit portions 17a to 17c, buffer memory portions 18a to 18c, and an arithmetic circuit portion 19.

The light-receiving signals outputted from each of the light-sensitive elements 15d to 15f are inputted to the height position detecting circuit portions 16a to 16c. The height position detecting circuit portions 16a to 16c output analog information on X-direction and analog information on Y-direction relative to the light-receiving reference position Q0 based on each of the inputted light-receiving signals. The analog/digital converting circuit portions 17a to 17c convert the X-direction analog information and the Y-direction analog information into digital, and output the digitalized X-direction information and the Y-direction information to the buffer memory portions 18a to 18c as digital signals. The digitalized X-direction information and the Y-direction information are inputted to the arithmetic circuit portion 19 through the buffer memory portions 18a to 18c.

Since the area sensor is used for each of the light-sensitive elements 15d to 15f, it is possible to obtain three-dimensional light amount distribution information of the surface of the wafer 2. The light amount distribution information of each of the area sensors are inputted into the arithmetic circuit portion 19. Therefore, information regarding the degrees of blur (the coarse surface information) and peak information of the reflection lights P6' to P8' of the irradiation lights P6 to P8 reflected from the surface S of the wafer 2 are obtained.

In addition, encoder signals EN are inputted into the arithmetic circuit portion 19. A not-shown encoder outputs the encoder signals EN based on clock-pulse numbers according to a reference position of starting measurement of the wafer 2. The encoder signals EN are outputted at even intervals in time-series. Because the wafer 2 is rotated and is also delivered in a radial direction by the relative displacement means, the plane-coordinate-positions of the surface S as the detecting positions are decided in spirals based on the encoder signals EN.

The arithmetic circuit portion 19 correlates the plane-coordinate-positions to height information Z (the amount of deviation ΔZ from the reference height position Z1) and the coarse surface information in the detecting positions, and allows a memory portion 20 to store the height information Z and the coarse surface information.

Light-receiving signals of the photoelectric conversion elements 13a and 14a are inputted into an amplification circuit portion (AMP circuit portion) 21. Amplified signals of the amplification circuit portion 21 are converted from analog to digital (A/D conversion) by an analog/digital converting circuit portion 22, and the digitalized amplified signals are inputted into a peak detecting circuit 23 as digital signals.

Not only the A/D converted digital signals but also the encoder signals EN are inputted into the peak detecting circuit 23. The peak detecting circuit 23 correlates a peak position to plane-coordinate-position information based on the encoder signals EN, and outputs the correlated peak position to a calculation/synchronization circuit portion 24 as processing means (processor). The calculation/synchronization circuit portion 24 outputs a result of calculation to a memory portion 25 where peak position information for each of the irradiated detecting positions of the surface S are stored.

The calculation/synchronization circuit portion 24 sends and receives information between the memory portion 25 and the arithmetic circuit portion 19, to correct the plane-coordinate-positions stored in the memory portion 25 based on the plane-coordinate-position information stored in the memory portion 25, the height information Z (the amount of deviation ΔZ), information on the plane-coordinate-positions and the coarse surface information which are stored in memory portion 20. A well-known formula may be used to correct the plane-coordinate positions, such as the formula described in the foregoing.

Then, the calculation/synchronization circuit portion 24 displays detected positions of the foreign substance (flaw) 10 on a display portion 26 based on the corrected plane-coordinate-positions and the peak position information according to a result of correction.

Therefore, according to the embodiment of the present invention, because it is possible to analyze and process the amount of deviation from the reference height position Z1 of the irradiated detecting positions even when the surface S of the wafer 2 is coarse, it is possible to reduce the time and labor in obtaining accuracy of adjustment of a stage structuring a part of the relative displacement means and on which the wafer 2 is mounted.

Also, according to the embodiment of the present invention, since the reflection lights P6' to P8' disappear sequentially in an edge or a curb of the wafer 2, it is possible to measure the wafer 2 until its edge or the curb. In addition, it is also possible to specify positions of an orientation flat 2A and a notch 2B (which are shown in FIG. 4) of the wafer 2 from a relation between the disappearance of the reflection lights P6' to P8' and the plane-coordinate positions.

Therefore, according to the surface inspection apparatus of the present invention, it is possible to distinguish whether or not the irradiated detecting position for the foreign substance or the flaw or the like existing on the surface of the inspecting object is deviated from the reference height even when the surface of the inspecting object is coarse and even if there is a distortion in the surface, and also, it is possible to detect the amount of deviation from the reference height position even when the surface of the inspecting object is coarse by removing an influence of such coarseness. Therefore, even when the surface of the inspecting object is coarse, it is possible to remove the influence of the coarseness of the surface, and to obtain the plane-coordinate position as the detecting position of the foreign substance (flaw) accurately by correcting the plane-coordinate position.

Figure 10A:
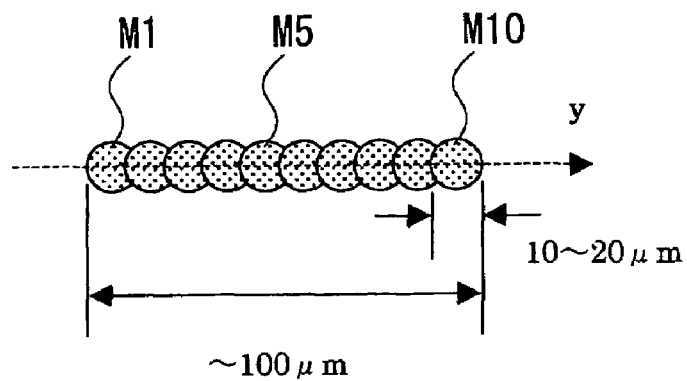
Figure 10B:
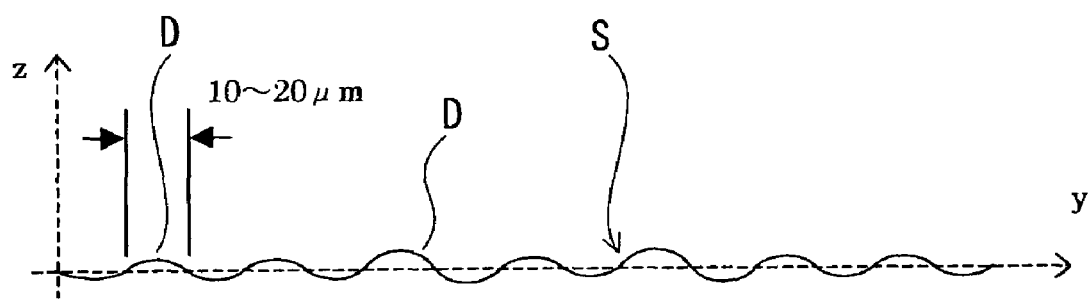
Figure 10C:
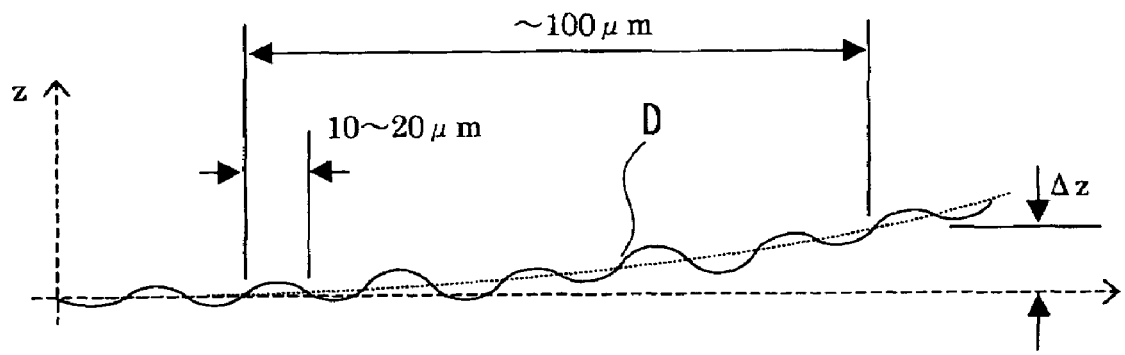

FIGS. 10A to 10C are explanatory diagrams for explaining another embodiment of the surface inspection apparatus according to the present invention. In the present embodiment, multiple beams including 10 (ten) spots M1 to M10 each having a same spot diameter with respect to each other are configured to be irradiated on the surface S of the wafer 2 as shown in FIG. 10A.

The multiple beams are irradiated on the surface S in such a manner that the neighboring spots among the spots M1 to M10 of the multiple beams are overlapped partially to each other. A size of the spot diameter is, for example but not limited to, approximately 10 to 20 micrometers, and thus length of alignment of the multiple beams from one end to the other end is, for example but not limited to, 100 micrometers.

When such multiple beams are irradiated on the surface S of the wafer 2, it is possible to detect a surface distortion D on the wafer 2 having a scale of lower than 100 micrometers, as shown in FIGS. 10B and 10C.

The surface distortion D occurs when the wafer 2 is rotated at high speed. Historically, the surface distortion D has been disregarded in a conventional surface inspection, since the surface distortion D is microscopic as compared with the warpage that normally occurs with a scale of more than 100 micrometers and thus it is not so influential.

However, high-resolution performance for detecting even more microscopic foreign substance, thinning in the wafer 2, and even higher speed for rotating the wafer 2 to realize high throughput, are called for in recent years. Accordingly, a microscopic surface distortion D caused by a stationary wave vibration or a bias in a torque due to the high rotation of the wafer 2 is expected to become actual.

Therefore, by configuring an analysis/process program in the recording unit/processor to be able to detect the surface distortion D, it is possible to analyze information on state of the surface S (state information) including not only the coarse surface information but also surface distortion information. Accordingly, it is possible to carry out a surface inspection with higher accuracy.

As well as in this embodiment, it is possible to distinguish whether or not the irradiated detecting position for the foreign substance or the flaw or the like existing on the surface of the inspecting object is deviated from the reference height even when the surface of the inspecting object is coarse and even if there is the distortion in the surface, and also, it is possible to detect the amount of deviation from the reference height position even when the surface of the inspecting object is coarse by removing an influence of such coarseness. Therefore, even when the surface of the inspecting object is coarse, it is possible to remove the influence of the coarseness of the surface, and to obtain the plane-coordinate position as the detecting position of the foreign substance (flaw) accurately by correcting the plane-coordinate position.

Although the present invention has been described in terms of exemplary embodiments, it is not limited thereto. Rather, the appended claims should be construed broadly to include other variants and embodiments of the invention which may be made by those skilled in the field of this art without departing from the scope and range of equivalents of the invention.

What is claimed is:

1. A surface inspection apparatus, comprising:
   an optical system including an irradiation optical unit and a light-receiving optical unit; said irradiation optical unit being adapted for irradiating irradiation light emitted from a light source onto a surface of an object to be inspected and said light-receiving optical unit being adapted for receiving scattered light of the irradiation light reflected from the surface of said object;
   a displacement mechanism for displacing a position to be irradiated and detected by said optical system on the surface of said object relative to said optical system;
   a recording unit for detecting a state of the surface of said object based on a result of light-receiving of said optical system and recording the irradiated and detected position on the surface of said object as a plane-coordinate-position;
   a detector for detecting an amount of deviation of said plane-coordinate-position in a height direction relative to a reference height position;
   a first processor for correcting the plane-coordinate-position as said irradiated and detected position based on the deviation amount detected by said detector and thereby obtaining said corrected plane-coordinate-position;
   said irradiation optical unit comprises a multibeam irradiation optical unit for converging and irradiating multiple beams of which optical axes of irradiation are mutually parallel upon the surface of said object;
   said detector comprises a light-condensing optical unit including light-sensitive elements which have mutually parallel light-receiving axes and which are adapted for respectively receiving said multiple beams reflected by the surface of said object; and
   a second processor which analyzes information on said state of the surface as to whether the surface has a rough surface based on the results of receiving of said multiple beams, which obtains the plane-coordinate-position of said irradiated and detected position at the reference height position based on a difference between light-receiving reference positions of each of said light-sensitive elements when assumed that the irradiated and detected position of said object is at the reference height position and actual light-receiving positions of each of said light-sensitive elements, according to a result of the analysis of the surface state information, and which causes the first processor to correct the plane-coordinate-position.

2. The surface inspection apparatus according to claim 1, wherein said displacement mechanism comprises a rotational driving mechanism for rotating said object and a linear movement mechanism for linearly moving said object in a radial direction of the object, said irradiation optical axes are aligned in parallel in said radial direction of the object, and said light-receiving axes of said light-sensitive elements are aligned symmetrical to said irradiation optical axes in such a manner as to sandwich center of rotation of said object.

3. The surface inspection apparatus according to claim 1, wherein each of said light-sensitive elements is structured by an area sensor.

4. The surface inspection apparatus according to claim 2, wherein each of said light-sensitive elements is structured by an area sensor.

5. The surface inspection apparatus according to claim 1, wherein said surface state information includes information on a surface distortion of said object.

6. The surface inspection apparatus according to claim 2, wherein said surface state information includes information on a surface distortion of said object.

7. The surface inspection apparatus according to claim 1, further comprising a display, wherein said processor displays a position at which a foreign substance and/or flaw is detected on the surface of the object on said display, based on the corrected plane-coordinate-position according to a result of correction.

8. The surface inspection apparatus according to claim 1, wherein said multiple beams including a plurality of spots each having a same diameter of approximately 10 to 20 micrometers to each other are irradiated on the surface of the object in such a manner that neighboring spots of said plurality of spots are partially overlapped to each other, and length of alignment of said multiple beams from one end to the other end are approximately 100 micrometers or less.

9. A surface inspection apparatus, comprising:
   an irradiation optical system including a plurality of light sources, the irradiation optical system being configured to converge and irradiate a plurality of irradiation light beams each irradiated from one of the corresponding plurality of light sources, as multiple beams in which optical axes of irradiation thereof are mutually parallel, toward a mutually different plurality of parts on a surface of an object to be inspected;
   a displacement mechanism configured to displace positions of the plurality of parts on the surface of the object irradiated by the irradiation optical system as irradiated-detected positions;
   a light-receiving optical system configured to receive scattered light of the plurality of irradiation light beams irradiated from the irradiation optical system and reflected by the surface of the object;
   a recording unit configured to detect a state of the surface of the object based on an output of receiving of the scattered light by the light-receiving optical system to obtain the irradiated-detected positions, and configured to record the obtained irradiated-detected positions as plane-coordinate-positions;

a light-condensing optical system including a plurality of light-sensitive elements, each of the light-sensitive elements being provided correspondingly to corresponding one of the plurality of irradiation light beams, each of the plurality of light-sensitive elements having a light-receiving axis parallel to each other and configured to receive one of the plurality of irradiation light beams reflected by the plurality of parts on the surface of the object, and each of the light-sensitive elements including a light-receiving reference position as a position for receiving corresponding one of the plurality of irradiation light beams when corresponding one of the plane-coordinate positions of the object is at a reference height position;

a detector configured to detect a difference between the light-receiving reference position of each of the plurality of light-sensitive elements and an actual light-receiving position of corresponding one of the plurality of irradiation light beams received by each of the light-sensitive elements; and a processor configured to analyze whether the surface of the object includes a rough surface based on the differences between the light-receiving reference positions of the respective plurality of light-sensitive elements and the actual light-receiving positions of the respective plurality of light-sensitive elements detected by the detector.

10. The surface inspection apparatus according to claim 9, wherein the processor is further configured to obtain the plane-coordinate positions of the irradiated-detected positions at the reference height position, based on a result of analysis of whether the surface of the object includes the rough surface and the differences between the light-receiving reference positions of the respective plurality of light-sensitive elements and the actual light-receiving positions of the respective plurality of light-sensitive elements detected by the detector.

11. The surface inspection apparatus according to claim 10, wherein the processor is further configured to correct the plane-coordinate positions recorded in the recording unit, based on the plane-coordinate positions of the irradiated-detected position at the reference height position obtained.

12. The surface inspection apparatus according to claim 9, wherein the displacement mechanism comprises a rotational driving mechanism configured to rotate the object and a linear movement mechanism configured to linearly move the object in a radial direction of the object, the irradiation optical axes are aligned in parallel in the radial direction of the object, and the light-receiving axes of the light-sensitive elements are aligned symmetrical to the irradiation optical axes in such a manner as to sandwich center of rotation of the object.

13. The surface inspection apparatus according to claim 9, wherein each of the light-sensitive elements includes an area sensor.

14. The surface inspection apparatus according to claim 10, wherein each of the light-sensitive elements includes an area sensor.

15. The surface inspection apparatus according to claim 9, wherein the processor is further configured to analyze whether the surface of the object includes a surface distortion based on the differences between the light-receiving reference positions of the respective plurality of light-sensitive elements and the actual light-receiving positions of the respective plurality of light-sensitive elements detected by the detector.

16. The surface inspection apparatus according to claim 10, wherein the processor is further configured to analyze whether the surface of the object includes a surface distortion based on the differences between the light-receiving reference positions of the respective plurality of light-sensitive elements and the actual light-receiving positions of the respective plurality of light-sensitive elements detected by the detector.

17. The surface inspection apparatus according to claim 11, further comprising a display, wherein said processor is further configured to display a position at which a foreign substance and/or flaw is detected on the surface of the objection the display, based on the corrected plane-coordinate-position according to a result of correction.

18. The surface inspection apparatus according to claim 9, wherein the multiple beams including a plurality of spots each having a same diameter of approximately 10 to 20 micrometers to each other are irradiated on the surface of the object in such a manner that neighboring spots of the plurality of spots are partially overlapped to each other, and length of alignment of the multiple beams from one end to the other end are approximately 100 micrometers or less.

* * * * *